United States Patent [19] [11] Patent Number: 6,060,642
Tecott et al. [45] Date of Patent: May 9, 2000

[54] SEROTONIN 5-HT6 RECEPTOR KNOCKOUT MOUSE

[75] Inventors: Laurence H. Tecott, San Francisco; Thomas J. Brennan, San Carlos, both of Calif.

[73] Assignee: The Regents of the University of California, Oakland, Calif.

[21] Appl. No.: 09/132,388

[22] Filed: Aug. 11, 1998

Related U.S. Application Data

[60] Provisional application No. 60/055,817, Aug. 15, 1997.

[51] Int. Cl.[7] .............................. C12N 5/00; C12N 15/12; A01K 67/027; G01N 33/15; C07H 21/04
[52] U.S. Cl. ................................. 800/3; 800/18; 800/21; 800/9; 435/172.1; 435/172.3; 435/325; 435/455; 536/23.5
[58] Field of Search .................................. 800/3, 18, 21, 800/9; 435/455, 172.1, 172.3, 325; 536/23.5

[56] References Cited

U.S. PATENT DOCUMENTS 5,698,766  12/1997  Julius et al. ................................. 800/2

OTHER PUBLICATIONS

Boss, F.G., et al., "Functional and Radioligand Binding Characterization of Rat 5–HT$_6$ Receptors Stably Expressed in HEK293 Cells," *Neuropharmacology* (1997) vol. 36, No. (4/5):713–720.

Bourson, Anne, et al., "Determination of the Role of the 5–HT$_6$ Receptor in the Rat Brain: A Study Using Antisense Oligonucleotides[1]," *The Journal of Pharmacology and Experimental Therapeutics* (1995) vol. 274, No. (1):173–180.

Brennan, Thomas J., et al., "Sound–Induced Seizures In Serotonin 5–HT$_{2C}$ Receptor Mutant Mice," *Nature Genetics* (Aug. 1997) vol. 16:387–390.

Kohen, Ruth, et al., "Cloning, Characterization, and Chromosomal Localization of A Human 5–HT$_6$ Serotonin Receptor," *Journal of Neurochemistry* (1996) vol. 66, No. (1):47–56.

Pierce, P.A., et al., "5–Hydroxytryptamine Receptor Subtype Messenger RNAs In Rat Peripheral Sensory And Sympathetic Ganglia: A Polymerase Chain Reaction Study," *Neuroscience* (1996) vol. 70, No. (2):553–559.

Roth, Bryan L., et al., "Binding of Typical and Atypical Antipsychotic Agents 5–Hydroxytryptamine–6 and 5–Hydroxytryptamine–7 Receptors[1]," *The Journal Of Pharmacology and Experimental Therapeutics* (1994) vol. 268, No. (3):1403–1410.

Ruat, Martial, et al., "A Novel Rat Serotonin (5–HT$_6$) Receptor: Molecular Cloning, Localization And Stimulation Of cAMP Accumulation," *Biochemical and Biophysical Communications Research Communications* (May 28, 1993) vol. 193, No. (1):268–276.

Saudou, Frédéric, et al., "5–Hydroxytryptamine Receptor Subtypes In Vertebrates And Invertebrates," *Neurochem Int.* (1994) vol. 25, No. (6):503–532.

Sleight, A.J., et al., "Effects of Altered 5–HT$_6$ Expression In The Rat: Functional Studies Using Antisense Oligonucleotides," *Behavioural Brain Research* (1996) vol. 73:245–248.

Tecott, Laurence H., et al., "Behavioral Genetics: Genes And Aggressiveness," *Current Biology* (1996) vol. 6, No. (3):238–240.

Ward, Raymond P., et al., "Colocalization of Serotonin Receptor Subtypes 5–HT2A, 5–HT2C, and 5–HT6 With Neuropeptides In Rat Striatum," *The Journal Of Comparative Neurology* (1996) vol. 370:405–414.

Bradley et al., Bio/Technology, 10:534–539, 1992.

Saudou et al., Science, 265:1875–1878, 1994.

Kohen et al., GenBank Accession #L41146, 1996.

Kohen et al., GenBank Accession #L41147, 1996.

*Primary Examiner*—Deborah Crouch
*Assistant Examiner*—Janet M. Kerr
*Attorney, Agent, or Firm*—Pamela J. Sherwood; Paula A. Borden; Bozicevic, Field & Francis, LLP

[57] ABSTRACT

The present invention features transgenic mice models for gene function, wherein the transgenic mice are characterized by having altered serotonin 5-HT6 receptor gene function. The transgenic mice may be either homozygous or heterozygous for a disruption in the endogenous 5-HT6 gene. Transgenic mice homozygous for a disruption in the endogenous 5-HT6 gene display a phenotype of increased anxiety behavior including diminished investigation of foreign objects and an elevation in stretched attend postures.

3 Claims, 1 Drawing Sheet

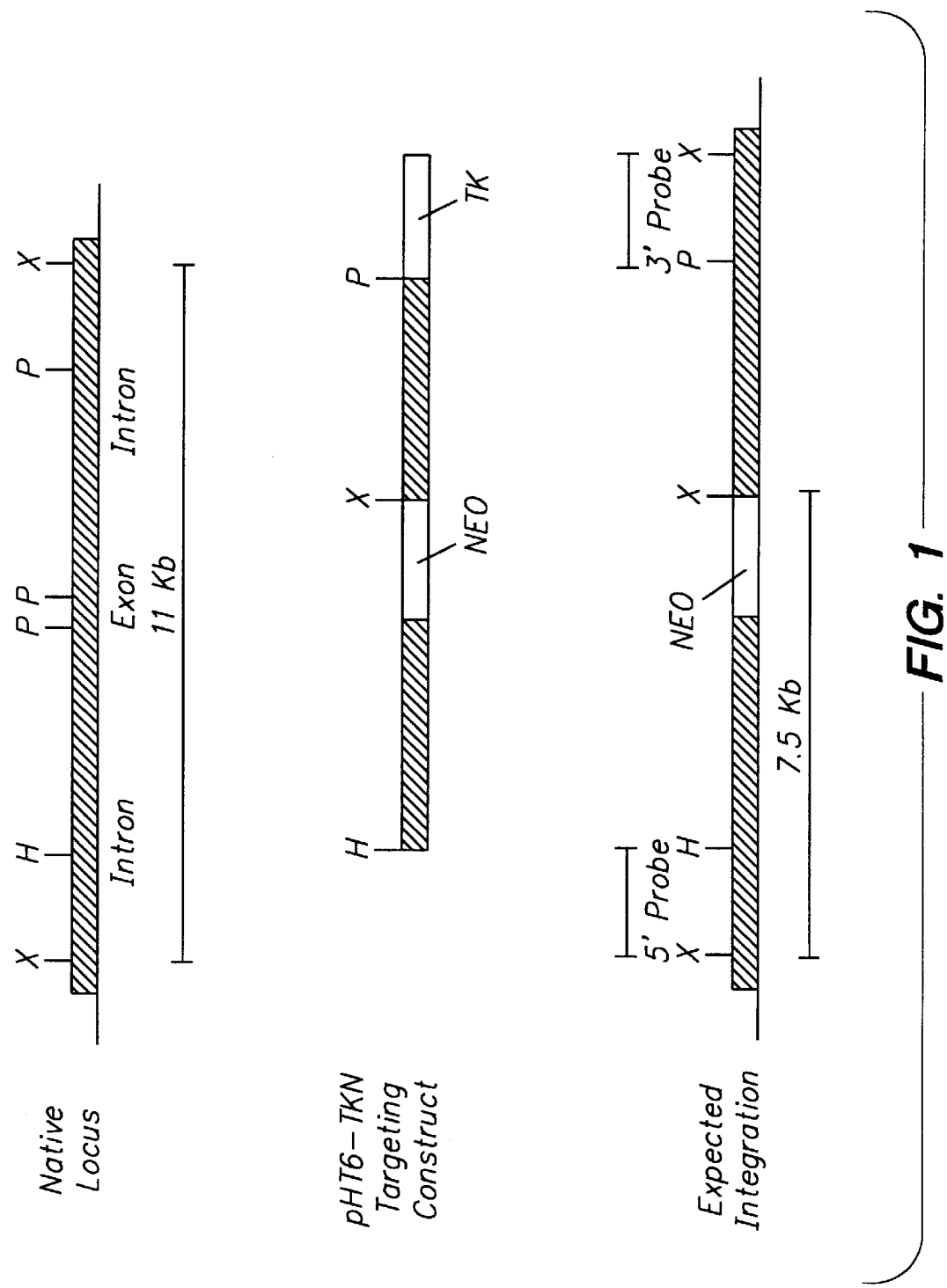

SEROTONIN 5-HT6 RECEPTOR KNOCKOUT MOUSE

This application claims the benefit of U.S. Provisional Application Ser. No. 60/055,817, filed Aug. 15, 1997.

This invention was made with Government support under Grant no. DA00282, awarded by the National Institutes of Health. The Government has certain rights in this invention.

INTRODUCTION

Background

The biogenic amine serotonin (5-hydroxytryptamine; 5-HT) is a brain neurotransmitter that has been strongly implicated in the pathophysiology and treatment of a wide variety of neuropsychiatric disorders. It exerts its effects through a diverse family of serotonin receptor subtypes. Of the 14 different mammalian serotonin receptors to have been cloned, all but one are members of the G-protein coupled receptor superfamily. Several of these, including the serotonin 5-HT6 receptor, stimulate adenylyl cyclase via G coupling. 5-HT6 has a high affinity for several therapeutically important antidepressant, antianxiety, hallucinogenic and antipsychotic drugs, particularly the atypical antipsychotics such as clozapine. The relevance of the 5-HT6 receptor to psychotherapeutics is indicated both through its unique anatomical distribution and pharmacological properties.

Messenger RNA encoding the 5-HT6 receptor has been localized by in situ hybridization histochemistry to brain regions that regulate emotional responses, cognition and motor function. This distribution pattern is generally matched by the localization of the 5-HT6 receptor protein identified by specific antibodies. This distribution is consistent with the binding of psychoactive drugs. Therefore, 5-HT6 receptors are implicated in the etiology of major psychiatric disorders and in the actions of psychiatric drugs.

Antipsychotic medications are the treatment of choice for schizoaffective disorders. Evidence to date suggests that all of the antipsychotic drugs (except clozapine) are similarly effective in treating psychoses, with the differences being in milligram potency and side effects. Sometimes patients view the side-effects of the antipsychotic drugs as being worse than their original psychosis. These include acute dystonic reactions, akathisia, Parkinsonism, in which akinesia is a key feature, and tardive dyskinesia. Clozapine (Clozaril) has been proven to be more effective than all other antipsychotic drugs in treating certain disorders. It has reduced movement side-effects, but other serious side-effects limit its use. In rare cases coma and death may result from the drug treatment.

The importance of psychoactive drugs in present treatment of mental illness, and the presence of serious and undesirable side-effects with their use, makes the development of improved drugs of great interest. Animal models useful in screening assays provide a benefit by determining candidate agents that have improved specificity of action.

Relevant Literature

An overview of 5-hydroxytryptamine receptor subtypes in vertebrates and invertebrates may be found in Saudou and Hen (1994) *Neurochem Int* 25:503–532. The cloning, characterization, and chromosomal localization of a human 5-HT6 serotonin receptor is described in Kohen et al. (1996) *J Neurochem* 66:47–56.Aug. 8, 1997. The human 5-HT6 polypeptide sequence diverged significantly from that published for the rat receptor. It was determined that the published rat sequence contained a frame shift error. The gene for the receptor maps to the human chromosome region 1p35–p36. Molecular cloning of the rat receptor is described in Ruat et al. (1993) *Biochem Biophys Res Commun* 193:268–276.

Boess et al. (1997) *Neuropharmacology* 36:713–720, stably expressed the rat 5-HT6 receptor in HEK293 cells and compared the affinity of a range of compounds in competition binding experiments. The observed binding was LSD>omega-N-methyl-5-HT=bufotenine=5-methoxytryptamine>5-HT>2-methyl-5-HT=5-benzyloxytryptamine=tryptamine>5-carboxamidotryptamine>>5-HTQ. Receptor antagnosists include methiothepin, clozapine, mianserin and ritanserin. The binding of typical and atypical antipsychotic agents to 5-HT6 and 5-HT7 receptors is discussed in Roth et al. (1994) *J Pharmacol Exp Ther* 268:1403–1410. Clozapine and several related atypical antipsychotic agents (rilapine, olanzepine, tiospirone, fluperlapine, clorotepine and zotepine) had high affinities for 5-HT6 receptor. Several dopamine-selective antipsychotic agents (raclopride, rimcazole and penfluridol) had essentially no affinity for either the 5-HT6 or 5-HT7 receptors.

Ward and Dorsa (1996) *J Comp Neurol* 370:405–414 describe the striatal distribution of the mRNAs of the serotonin2A (5-HT2A), serotonin2C (5-HT2C), and serotonin6 (5-HT6) receptors in relation to enkephalin, substance P, and dynorphin expressing output neurons. Pierce et al. (1996) *Neuroscience* 70:553–559 assayed for the presence of messenger RNA for rat serotonin receptor subtypes in peripheral sensory and sympathetic ganglia was detected using the method of polymerase chain reaction. The presence of messenger RNA for 5-HT6 receptor was found within superior cervical ganglia, but not lumbar sympathetic ganglia.

The effects of administering 5-HT6 antisense oligonucleotides to the rat brain are described in Sleight et al. (1996) *Behav Brain Res* 73:245–248; and Bourson et al. (1995) *J Pharmacol Exp Ther* 274:173–180. A behavioral syndrome of yawning, stretching and chewing was observed in treated rats.

SUMMARY OF THE INVENTION

Non-human transgenic animal models are provided for serotonin 5-HT6 receptor (5-HT6) function, where the transgenic animal is characterized by having an altered 5-HT6 gene. Alterations to the gene include deletions or other loss of function mutations, introduction of an exogenous gene having a nucleotide sequence with targeted or random mutations, introduction of an exogenous gene from another species, or a combination thereof. The transgenic animals may be either homozygous or heterozygous for the alteration. The animals and cells derived therefrom are useful for screening biologically active agents that may modulate 5-HT6 receptor function. The screening methods are of particular use for determining the specificity and action of antianxiety, antidepressant or antipsychotic drugs, particularly serotoninergic drugs, or drugs that may interact with serotonin receptors. The animals are useful as a model to investigate the role of serotonin 5-HT6 receptors in normal brain function.

BRIEF DESCRIPTION OF THE DRAWINGS

FIG. 1 is a diagram showing sequences for introduction of a targeted mutation into the 5-HT6 receptor gene. Restriction maps of the native 5-HT6 receptor gene locus, the pHT6-TKN targeting construct, and the gene following homologous recombination are shown. H: Hind III; NEO: neomycin resistance cassette; P: Pst I; TK: thymidine kinase gene; X: Xba I.

DATABASE REFERENCES FOR GENETIC SEQUENCES

The human serotonin 5-HT6 receptor gene has the Genbank accession number L41146. The rat serotonin 5-HT6 receptor gene has the Genbank accession number L41147.

DESCRIPTION OF THE SPECIFIC EMBODIMENTS

Non-human transgenic animal models useful for screening psychoactive drugs are provided. The animals have genetically altered serotonin 5-HT6 receptors. Alterations to the gene include deletion or other loss of function mutations, introduction of an exogenous gene having a nucleotide sequence with targeted or random mutations, introduction of an exogenous gene from another species, or a combination thereof. The transgenic animals may be either homozygous or heterozygous for the genetic alteration.

The subject animals are useful for testing the specificity of drugs developed as 5-HT6 receptor-selective agonists and antagonists. Completely selective compounds will not interact with other receptors, and thus will be inert in 5-HT6 knockout mice. In addition, these animals provide a useful model for the behavioral testing of psychoactive compounds. Antipsychotic, antidepressant and antianxiety drugs can be assayed by behavioral testing appropriate to each class of drugs. The animals are also used to determine the extent to which 5-HT6 receptors contribute to the efficacy of drugs in current use.

TRANSGENIC ANIMALS

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins". In the present invention, knockouts have a partial or complete loss of function in one or both alleles of the endogenous 5-HT6 gene. Knockins have an introduced transgene with altered genetic sequence and function from the endogenous gene. The two may be combined, such that the naturally occurring gene is disabled, and an altered form introduced.

In a knockout, preferably the target gene expression is undetectable or insignificant. A knock-out of a 5-HT6 gene means that function of the 5-HT6 receptor has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of 5-HT6 genes. A functional knock-out may also be achieved by the introduction of an anti-sense construct that blocks expression of the native genes (for example, see Li and Cohen (1996) Cell 85:319–329). "Knock-outs" also include conditional knockouts, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of the native 5-HT6 gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. The introduced sequence may encode a 5-HT6 polypeptide, or may utilize the 5-HT6 promoter operably linked to a reporter gene. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

Specific constructs of interest, but are not limited to, include anti-sense 5-HT6, which will block native 5-HT6 expression, expression of dominant negative 5-HT6 mutations, and over-expression of a 5-HT6 gene. A detectable marker, such as lac Z may be introduced into the locus, where upregulation of expression will result in an easily detected change in phenotype. Constructs utilizing the 5-HT6 promoter region, in combination with a reporter gene or with the coding region are also of interest.

A series of small deletions and/or substitutions may be made in the 5-HT6 gene to determine the role of different exons in DNA binding, transcriptional regulation, etc. By providing expression of 5-HT6 protein in cells in which it is otherwise not normally produced, one can induce changes in cell behavior.

DNA constructs for homologous recombination will comprise at least a portion of the 5-HT6 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

5-HT6 NUCLEIC ACID COMPOSITIONS

The terms "serotonin 5-HT6 receptor gene" is used generically to designate serotonin 5-HT6 receptor genes, e.g. homologs from rat, human, mouse, guinea pig, etc., and their alternate forms. The gene is also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding 5-HT6 receptor may be cDNA or genomic DNA or a fragment thereof. The gene may be introduced into an appropriate vector for extrachromosomal maintenance or for integration into the host.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where serotonin 5-HT6 receptor is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1:194–205; Mortlock et al. (1996) *Genome Res.* 6:327–33; and Joulin and Richard-Foy (1995) *Eur J Biochem* 232:620–626.

The regulatory sequences may be used to identify cis acting sequences required for transcriptional or translational regulation of 5-HT6 receptor expression, especially in different tissues or stages of development, and to identify cis acting sequences and trans acting factors that regulate or mediate expression. Such transcription or translational control regions may be operably linked to a 5-HT6 receptor gene in order to promote expression of wild type or altered 5-HT6 or other proteins of interest in cultured cells, or in embryonic, fetal or adult tissues, and for gene therapy.

The nucleic acid compositions used in the subject invention may encode all or a part of the 5-HT6 receptor polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Homologs of cloned serotonin 5-HT6 receptor are identified by various methods known in the art. Nucleic acids having sequence similarity are detected by hybridization under low stringency conditions, for example, at 50° C. and 10x SSC (0.9 M saline/0.09 M sodium citrate) and remain bound when subjected to washing at 55° C. in 1x SSC. Sequence identity may be determined by hybridization under stringent conditions, for example, at 50° C. or higher and 0.1x SSC (9 mM saline/0.9 mM sodium citrate). By using probes, particularly labeled probes of DNA sequences, one can isolate homologous or related genes. The source of homologous genes may be any species, e.g. primate, rodents, canines, felines, bovines, ovines, equines, etc.

The 5-HT6 receptor sequence, including flanking promoter regions and coding regions, may be mutated in various ways known in the art to generate targeted changes in promoter strength, sequence of the encoded protein, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of 5-HT6 receptor polypeptides, or to alter properties of the proteins that affect their function or regulation.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

Drug Screening Assays

Through use of the subject transgenic animals or cells derived therefrom, one can identify ligands or substrates that bind to, modulate, antagonize or agonize 5-HT6 receptors. Screening to determine drugs that lack effect on these receptors is also of interest. Areas of investigation are the development of psychoactive therapies, e.g. antipsychotic, antianxiety, antidepressant, etc. treatments. Of particular interest are screening assays for agents that have a low toxicity for human cells.

A wide variety of assays may be used for this purpose, including in vivo behavioral studies, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cell derived therefrom. Cells may be freshly isolated from an animal, or may be immortalized in culture. Cell of particular interest include neural and brain tissue.

The term "agent" as used herein describes any molecule, e.g. protein or pharmaceutical, with the capability of affecting the biological action of serotonin 5-HT6 receptor. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening may be directed to known pharmacologically active compounds and chemical analogs thereof. Known antipsychotic drugs include the following. Drugs with a significant serotoninergic effect are of particular interest.

| Name | Class | Serotonergic Effect |
| --- | --- | --- |
| Chlorpromazine | Phenothiazine, Aliphatic | ++++ |
| Fluphenazine | Phenothiazine, Piperazine | + |
| Perphenazine | Phenothiazine, Piperazine | ++++ |
| Trifluoperazine | Phenothiazine, Piperazine | +++ |
| Thioridazine | Phenothiazine, Piperidine | ++++ |
| Mesoridazine | Phenothiazine, Piperidine | ++++ |
| Haloperidol | Butyrophenone | + |
| Clozapine | Dibenzodiazepine Atypical Agents | ++++ |
| Loxapine | Dibenzodiazepine | ++++ |
| Molindone | Dihydroindolone | + |
| Thiothixene | Thioxanthene | + |
| Risperidone | Benzisoxazole | 0 |

Known antidepressant drugs include the following. Of particular interest are serotonin-norepinephrine reuptake inhibitors, serotonin-receptor modulators and serotonin selective reuptake inhibitors.

| Generic Name | Trade Names | Class |
| --- | --- | --- |
| amitriptyline | Elavil, Endep | TCA |
| amoxapine | Asendin | Heterocyclic |
| bupropion | Wellbutrin | Other |
| clomipramine | Anafranil | TCA |
| desipramine* | Norpramin, Pertofrane | TCA |
| doxepin | Adapin, Sinequan | TCA |
| fluoxetine | Prozac | SSRI |
| fluvoxamine | Luvox | SSRI |
| imipramine | SK-Pramine, Tofranil, Janimine | TCA |
| isocarboxazid | Marplan | MAOI |
| maprotiline | Ludiomil | Heterocyclic |
| nefazodone | Serzone | SRM |
| nortriptyline* | Aventyl, Pamelor | TCA |
| paroxetine* | Paxil | SSRI |
| phenelzine | Nardil | MAOI |
| protriptyline | Vivactil | TCA |
| sertraline* | Zoloft | SSRI |
| tranylcypromine | Parnate | MAOI |
| trazodone* | Desyrel | SRM |
| trimipramine | Surmontil | TCA |
| venlafaxine | Effexor | SNRI |

MAOI = monoamine oxidase inhibitor
SNRI = Serotonin-norepinephrine reuptake inhibitor
SRM = serotonin-receptor modulator
SSRI = serotonin selective reuptake inhibitor
TCA = tricyclic antidepressant Known antianxiety drugs include the following.

| Generic Name | Brand Name |
| --- | --- |
| alprazolam | Xanax |
| chlordiazepoxide | Librium |
| clorazepate | Tranxene |
| diazepam | Valium |
| lorazepam | Ativan |
| oxazepam | Serax |
| prazepam | Centrax |
| triazolam | Halcion |
| buspirone | Buspar |
| chloral hydrate | Noctec, others |

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Antibodies specific for 5-HT6 receptor polymorphisms may be used in screening immunoassays, particularly to detect the binding of substrates to 5-HT6 receptors, or to confirm the absence or presence of a 5-HT6 receptor in a cell or sample. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and 5-HT6 receptor in a lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

A number of assays are known in the art for determining the effect of a drug on animal behavior. Behavioral abnormalities in animal models are useful for testing the effect, interactions, and specificity of a candidate biologically active agent. Some examples are provided, although it will be understood by one of skill in the art that many other assays may also be used. The subject animals may be used by themselves, or in combination with control animals. Control animals may have the native 5-HT6 receptor intact, or may be a combination transgenic, where the normal 5-HT6 gene is disrupted, and has been replaced with an exogenous gene, e.g. the human gene, a mutated mouse gene, etc.

Prepulse inhibition (PPI) of an acoustic startle response is impaired in schizophrenics. PPI can be studied in rodents, where a PPI deficit is introduced by drug treatment or conditions of social isolation. (See Varty and Higgins (1995) *Psychopharmacology* 122:15–26). The ability of neuroleptic drugs to restore a PPI disruption may be studied by inducing a deficit, and administering a candidate drug to determine if function is restored.

The ability of a candidate serotonin receptor antagonist to inhibit psychostimulant, e.g. amphetamine, cocaine, etc.—induced increases in extracellular levels of 5-HT or dopamine may be determined by in vivo microdialysis (see Kuroki et al. (1996) Brain Res. 743:357–361).

Memory and learning deficits are studied by various means, e.g. 3 runway panel for working memory impairment (attempts to pass through two incorrect panels of the three panel-gates at four choice points) (Ohno et al. (1997) *Pharmacol Biochem Behav* 57:257–261). Candidate drugs are assessed for their ability to restore or inhibit memory function. Anxiety testing in combination with drug therapy may be assessed with a variety of known tests, including elevated plus maze, light/dark box, fear potentiated startle responses, and the like.

Ethanol, cocaine, etc. can produce a significant increase in locomotor activity (LMA) in mice (Le, et al. (1997) Pharmacol Biochem Behav 57:325–332). Candidate drugs may be assessed for their ability to suppress this increase in locomoter activity. Candidate drugs may be assessed for the effect on self-administration by lever-pressing, etc. of drugs, e.g. cocaine, in rodent models.

The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a construct" includes a plurality of such constructs and reference to "the serotonin 5-HT6 receptor-encoding nucleic acid" includes reference to one or more serotonin 5-HT6 receptor-encoding nucleic acids and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Generation of 5-HT6 Receptor Mutant Mice

FIG. 1 depicts restriction maps of a portion of the mouse 5-HT6 receptor gene, the pHT6-TKN targeting construct, and the genetic alteration expected in a gene targeting event. The gene fragment was obtained from a strain 129 mouse P1 genomic library that was screened using PCR primers corresponding to the coding region of the rat 5-HT6 receptor. Alternatively, such a fragment is obtained by probing a strain 129 genomic phage library with a rat 5-HT6 receptor cDNA probe using publically available sequences.

The pHT6-TKN construct was made by deleting a 300 bp Pst I (P) restriction fragment from the coding region of the 5-HT6 receptor gene. The deleted region contained sequences encoding a region of the 5-HT6 receptor protein from the third transmembrane domain to the fifth intracellular loop. In its place, a neomycin resistance cassette (Neo) was inserted. The mutated fragment was subcloned into the pGK-TK plasmid, which contains the HSV thymidine kinase (TK) gene driven by the PGK promoter in a Bluescript vector.

Embryonic stem (ES) cells were electroporated with linearized pHT6-TKN vector, and then plated on fibroblast feeder layers. ES cells were treated with geneticin (neomycin analog) to select for cells that had incorporated the targeting construct. ES cell clones surviving drug selection were screened for homologous recombination events by Southern blot analysis. In the process of constructing the pHT6-TKN vector, an exogenous Xba I restriction site (X) was introduced at the 3' end of the Neo cassette. Therefore, ES cell genomic DNA was digested with Xba I and DNA blots were hybridized with a probe corresponding to a 5-HT6 receptor gene region located 5' to the integration site of the construct. With this strategy, the native allele is indicated by an 11 Kb band and a mutant allele produced by homologous recombination is indicated by a 7.5 Kb band (see FIG. 1).

ES cell clones with targeted 5-HT6 receptor gene mutations were then isolated, expanded, and used to generate chimeric mice. Chimeras were generated by microinjecting targeted ES cells into the cavities of blastocysts derived from the C57BL/6 mouse strain. Injected embryos were transferred into uteri of surrogate mothers, and chimeric mice were born. The chimeras were then bred with C57BL/6 mice, and germ line transmission of the targeted mutation was verified by Southern blots of DNA from the tails of the offspring. Crosses were then performed between male and female mice that were heterozygous for the targeted mutation. These crosses resulted in the production of offspring with the expected Mendelian ratios of sexes and genotypes. The absence of intact 5-HT6 receptor mRNA in homozygous mutant mice was verified by Northern blot analysis of brain RNA, using a probe corresponding to the deleted protein coding region. Homozygous mutant mice appear healthy.

Behavioral studies: 5HT6 receptor mutant and wild type littermate mice were acclimated to an open field enclosure (50×50×38 cm) in 3 daily 10 minute sessions. On the 4th day, a novel object (a small wooden block (approx 18×18× 36 mm)) was placed in the center of the field and the following behaviors observed: activity in the vicinity of the object, stretched attend postures (SAPs), and sniffs of the object.

A trend was present, with the knock-out animals displaying reduced sniffing of the object and elevated SAPs. The diminished investigation of the object, and elevation in SAPs, a "risk assessment" behavior, are both consistent with an elevation in trait anxiety in the mutant mice. For methodology, see Blanchard & Blanchard (1969) *J. Comp. Physiol. Psychol.* 67:370–375, "Crouching as an index of fear"; and Blanchard et al. (1990) *Psychopharmacol.* 101:511–518, "Diazepam changes risk assessment in an anxiety/defense test battery".

In another model of rodent anxiety, the elevated zero maze, knock-out animals displayed trends toward decreased exploration of the open arms and a significant elevation of stretched attend postures. These measures are also consistent with elevated anxiety (Shepherd et al. (1994) *Psychopharm.* 116:56–64, "Behavioural and pharmacological characterization of the elevated "zero-maze" as an animal model of anxiety"). These results, together with the known distribution of 5HT6 receptor expression in brain regions associated with anxiety, implicate 5HT6 receptors in the regulation of anxiety state.

What is claimed is:

1. A transgenic knock-out mouse comprising disruption in the endogenous serotonin 5-hydroxytryptamine 6 (5-HT6) receptor gene, wherein said disruption has been introduced into its genome by homologous recombination with a DNA targeting construct in an embryonic stem cell such that the targeting construct is stably integrated in the genome of said mouse, wherein the disruption of the 5-HT6 receptor gene results in an inability of said mouse to produce detectable levels of 5-HT6 receptor, and further wherein said mouse exhibits an elevation in anxiety behaviors relative to a non-transgenic control mouse.

2. The transgenic mouse of claim 1, wherein said disruption comprises a deletion of 5-HT6 receptor gene nucleotide sequences encoding a region of the mouse 5-HT6 receptor from the third transmembrane domain to the fifth intracellular loop.

3. A method for screening a candidate agent for the ability to reduce anxiety behavior in the transgenic mouse of claim 1 comprising:

(a) providing a first and a second transgenic mouse of claim 1;

(b) administering to said first transgenic mouse a candidate agent, and (c) comparing anxiety behavior of said first transgenic mouse of step (b) to the anxiety behavior of said second transgenic mouse of step (a) not administered said candidate agent; wherein a reduction in anxiety behavior in said first transgenic mouse administered said candidate agent relative to said second transgenic mouse not administered said candidate agent indicates that the candidate agent reduces anxiety behavior.

* * * * *